(12) United States Patent
Abizeid

(10) Patent No.: US 12,201,935 B2
(45) Date of Patent: Jan. 21, 2025

(54) DISINFECTANT, GAS ACCUMULATION AND COMBUSTION CONTROL DEVICE

(71) Applicant: Gabrielle Abizeid, Miami Beach, FL (US)

(72) Inventor: Gabrielle Abizeid, Miami Beach, FL (US)

( * ) Notice: Subject to any disclaimer, the term of this patent is extended or adjusted under 35 U.S.C. 154(b) by 585 days.

(21) Appl. No.: 17/525,848

(22) Filed: Nov. 12, 2021

(65) Prior Publication Data

US 2022/0072469 A1   Mar. 10, 2022

Related U.S. Application Data

(63) Continuation-in-part of application No. 16/994,909, filed on Aug. 17, 2020, now Pat. No. 11,473,794.

(51) Int. Cl.
| | |
|---|---|
| *B01D 53/02* | (2006.01) |
| *A61L 9/20* | (2006.01) |
| *B01D 53/04* | (2006.01) |
| *G01N 33/00* | (2006.01) |

(52) U.S. Cl.
CPC ............ *B01D 53/0454* (2013.01); *A61L 9/20* (2013.01); *B01D 53/0415* (2013.01); *G01N 33/0057* (2013.01); *A61L 2209/111* (2013.01); *A61L 2209/12* (2013.01); *B01D 2253/204* (2013.01); *B01D 2253/25* (2013.01); *B01D 2257/93* (2013.01); *B01D 2259/402* (2013.01)

(58) Field of Classification Search
CPC ........... A61L 2209/111; A61L 2209/16; A61L 9/014; A61L 9/20; A61L 2209/12; B01D 2257/70; B01D 2257/93; B01D 2259/4508; B01D 53/0407; B01D 53/0446; B01D 53/0454; B01D 2253/204; B01D 2253/25; B01D 2259/402; B01D 53/0415; F24F 11/77; F24F 2110/40; F24F 2110/65; F24F 8/10; F24F 11/0001; A01G 9/246; Y02B 30/70; G01N 33/0057; Y02A 40/25

See application file for complete search history.

(56) References Cited

U.S. PATENT DOCUMENTS

| | | | |
|---|---|---|---|
| 2014/0067130 A1* | 3/2014 | Pillai ........................ | A61L 9/00 315/297 |
| 2016/0054730 A1* | 2/2016 | Lou ......................... | F23N 5/022 700/51 |
| 2018/0154303 A1* | 6/2018 | Giles .................. | B01D 53/0454 |
| 2020/0408427 A1* | 12/2020 | Alsadah ................. | F24F 8/133 |
| 2022/0054699 A1* | 2/2022 | Nakama ................. | A61L 9/205 |
| 2023/0149578 A1* | 5/2023 | Igarashi ............... | A61N 5/0624 422/3 |

* cited by examiner

*Primary Examiner* — Christopher P Jones

(57) ABSTRACT

A gas accumulation and combustion control device combining a sorption system, a ventilation system, a control system, and sensor system, with the sensor system configured to detect gas contaminants, transmit a gas detection signal to the control system, the control system configured to adjust the ventilation system based on the gas detection signal, the ventilation system configured to draw the contaminated air in from the atmosphere and lead it toward the sorption system, which in turn is configured to adsorb or absorb the gas contaminants.

19 Claims, 15 Drawing Sheets

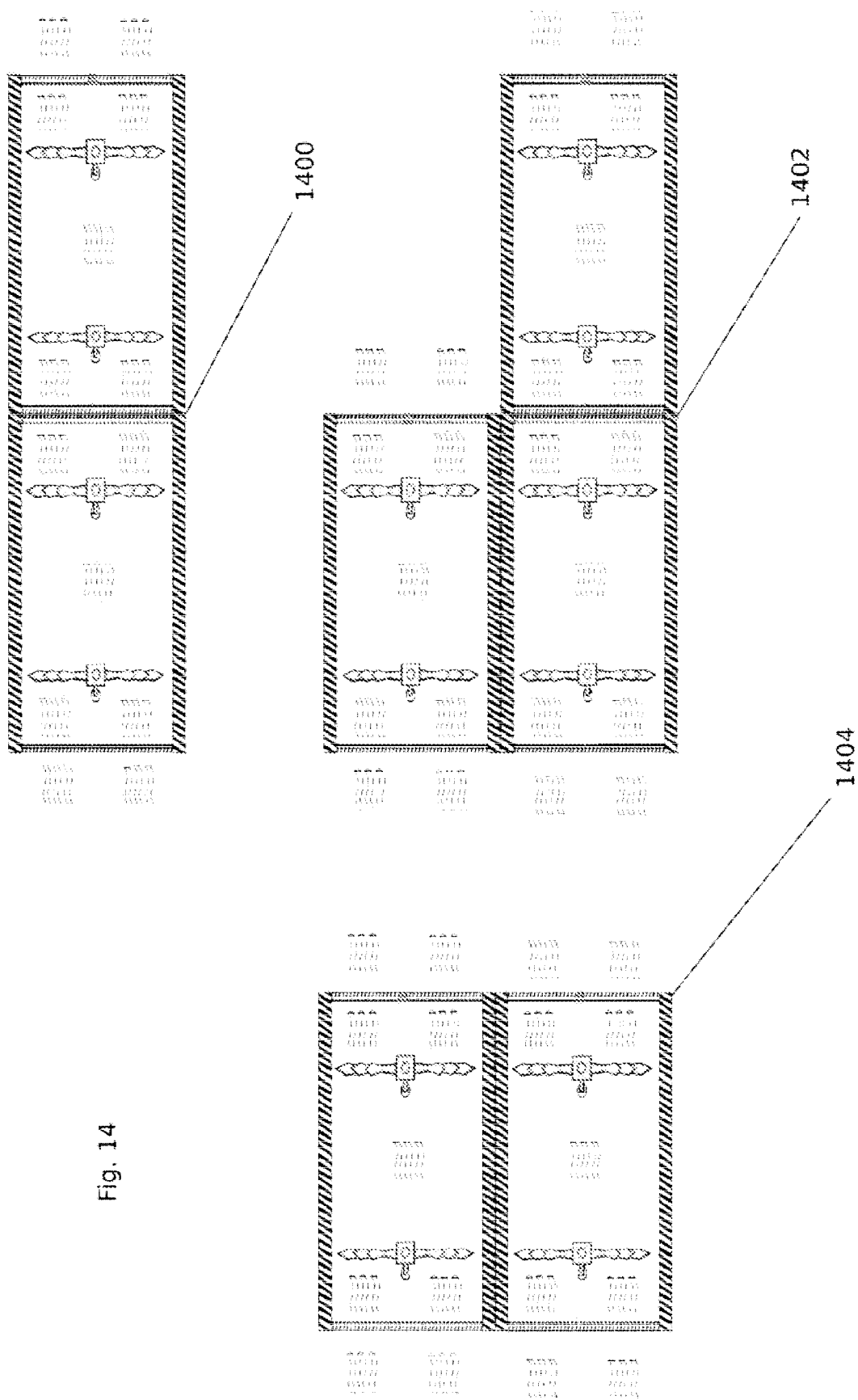

$$V_R \frac{dC_A}{dt} = s^{in} V_{EC} - k(C_{eq} g_{Ad} - C_A) V_{EC}$$

$$\frac{V_R}{k V_{EC}} \frac{dC_A}{dt} = \frac{s^{in}}{k} - C_{eq} g_{Ad} - C_A$$

$$C_A(t) = \left(\frac{s^{in}}{k} - g_{Ad} C_{eq} + C_{oA}\right) \cdot \left(e^{-\frac{V_{EC} \cdot k(t - t_1)}{V_R}}\right) - \frac{s^{in}}{k} + C_{eq} g_{Ad}$$

where $V_R$ = Volume of Room $V_{EC}$ = Volume of device?

$C_A$ = gas concentration in the room at time t $t$ = time of sorption $t_1$ = time the device is turned on for sorption $s^{in}$ = gas leak rate $k$ = rate of sorption $C_{eq}$ = sorption capacity $g_{Ad}$ = mass of sorption material prior to sorption $C_o$ = initial concentration of gas in the room

Fig. 15

DISINFECTANT, GAS ACCUMULATION AND COMBUSTION CONTROL DEVICE

PRIORITY

This application is a continuation-in-part of and claims priority to U.S. non-provisional application Ser. No. 16/994,909 filed Aug. 17, 2020. The referenced application is incorporated herein in its entirety as if restated in full.

BACKGROUND

The two main dangers of gas accumulation, whether in residential, commercial, laboratory, or industrial settings, include their flammability and their toxicity.

Fires are put out with great difficulty and expense, and cause damage not only to property, which can be extensive, but also to human (and animal) life. A gas fire is exceptionally dangerous, because gas not only burns but may combust, an effect which causes a sudden and massive spread of fire. Since gas is capable of squeezing through cracks or gaps and permeate through different surface, gas may spread from room to room in a manner much faster than traditional fires, which rely on solid media, such as wood. A gas fire is also easier to start than a traditional fire, since gas ignites instantly while solid media such as wood take longer. Further, since gas travels in a near random path, or else are blown about by even low-level currents, gas may enter areas where small fires would otherwise be acceptable due to their controlled nature and distance from more obviously flammable material, such as paper or wood. A person lighting a cigarette or a candle may not realize that they are triggering an explosion because of a stream of gas which has trickled in and accumulated in their room.

While the toxicity of gas generally does not affect property, it can be harmful, even lethal, to living organisms, such as people and animals. Even if a toxic gas is not flammable, the accumulation of gas, which is often undetected, may enter a living being's respiratory and circulatory system, killing otherwise healthy cells, particularly cells in the lungs, esophagus, nasal passage, and brain. Certain gases, such as carbon monoxide, may cause the types of damage described without even requiring a build-up, and such gases are immediately dangerous even in miniscule amounts.

Importantly, flammable and toxic gases are frequently odorless; and when they do have odors, those odors may be very faint. People have varying degrees of sensitivity to odors, and so gases that might be detected by one person may not be detected by another. Even if a person is sensitive to smells, the slow build up of gas may unconsciously adjust the person's sensitivity, such that a gas they would otherwise be detected may be undetected if the person has remained in the location during the gas build up.

What is needed is a device that can detect the presence of gas, isolate it through sorption, delay the negative effects of gas build-up through partial and/or continuous sorption, alert a location custodian of its presence, address a max sorption capacity event, and be easy to handle and control. Such a device may nullify the danger for small amounts of gas, or give an attended time to take remedial action, such as opening a window, calling the fire department, and/or evacuating the premises.

SUMMARY

The gas accumulation and combustion control device comprises a sorption box designed to hold a sorption system, a ventilation system, a sensor system, and a control system. The ventilation system is in electrical communication with the control system, which in turn is in informational communication with the sensor system.

The sorption box is essentially an enclosure against an atmosphere surrounding the sorption box. It has at least one or more passage walls, and one or more pass-through walls, which together form an internal cavity.

The pass-through walls are configured to permit air to flow between the cavity and the atmosphere, and the passage walls, which span from one pass-through wall to the other, is designed to contain the various systems.

The systems are configured to intelligently extract gas contaminants from the environment by actively accelerating air flow into the cavity and then absorbing or adsorbing the gas contaminants by means of sorption material.

BRIEF DESCRIPTION OF THE DRAWINGS

FIG. 14 show various configurations of multiple gas accumulation and combustion control devices.

FIG. 15 shows a number of equations that may be used to calculate the volume of the sorption box.

DETAILED DESCRIPTION

The gas accumulation and combustion control device is designed to prevent the accumulation of flammable and toxic gases in a residential, commercial, laboratory, or industrial setting.

Figure 1:
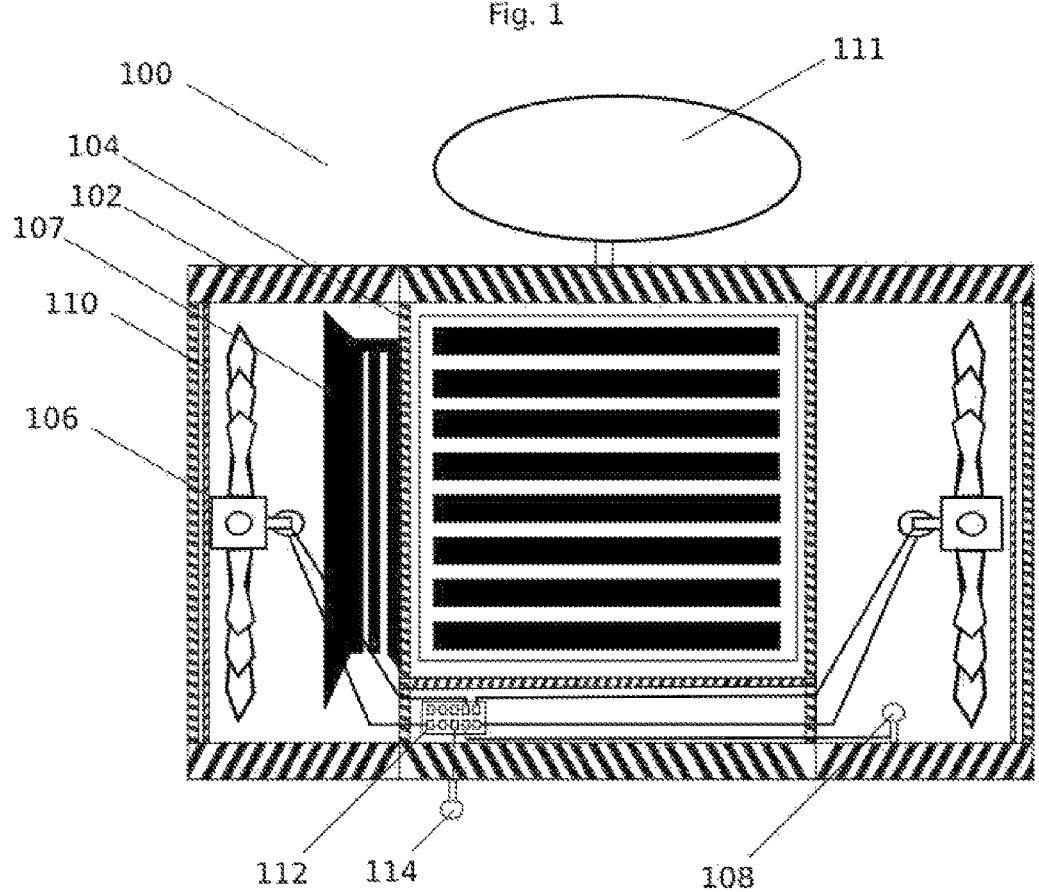
FIG. 1 shows a gas accumulation and combustion control device.

As shown in FIG. 1, the gas accumulation and combustion control device 100 comprises a sorption box 102, a sorption system 104, a ventilation system 106, a compressor 107, a pressure regulator 108, a dust filter 110, a control system 112, a gas collection container 111, and a sensor system 114. These components may be attached to each other mechanically, electrically, wirelessly, directly, and/or indirectly. The attachment may be permanent, temporary, removable, or replaceable.

Figure 2:
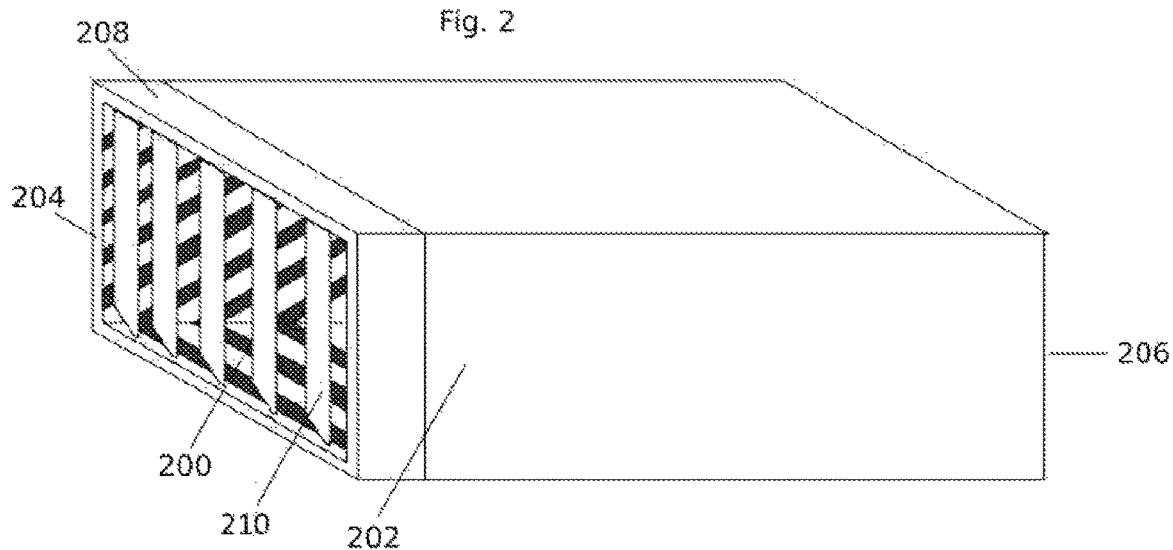
FIG. 2 shows a sorption box with pass-through walls.

The sorption box is an enclosure, preferably made of metal, such as aluminum or steel, a hard plastic, or a combination thereof. As shown in FIG. 2, the sorption box may be rectangular or tubular in shape and comprise a cavity 200 surrounded by one or more passage walls 202, and two pass-through walls, including one or more inlet walls 204 and one or more outlet walls 206, with the inlet and outlet walls configured to provide an inlet into and an outlet from the passage walls, respectively. The inlet and outlet walls may be grates in which air, particularly air mixed with flammable or toxic gases, and other small particles are permitted through while preventing entrance into the cavity by larger particles, such as those greater than 1 mm in diameter. In one variation, the inlet and outlet walls may each be coupled to inlet and outlet doors 208, respectively. The inlet and outlet doors may each comprise a set of shutters 210, the shutters oriented to permit fluid flow when in a substantially orthogonal orientation, to block fluid flow when in an orientation substantially in line with the doors, and to permit limited fluid flow when in an orientation between open and closed. The orientation may be controlled by the control system, which will be described below. The inlet and outlet doors may be slidably or hingedly attached to the inlet and outlet walls and configured to seal the inlet and outlet walls.

Figure 3:
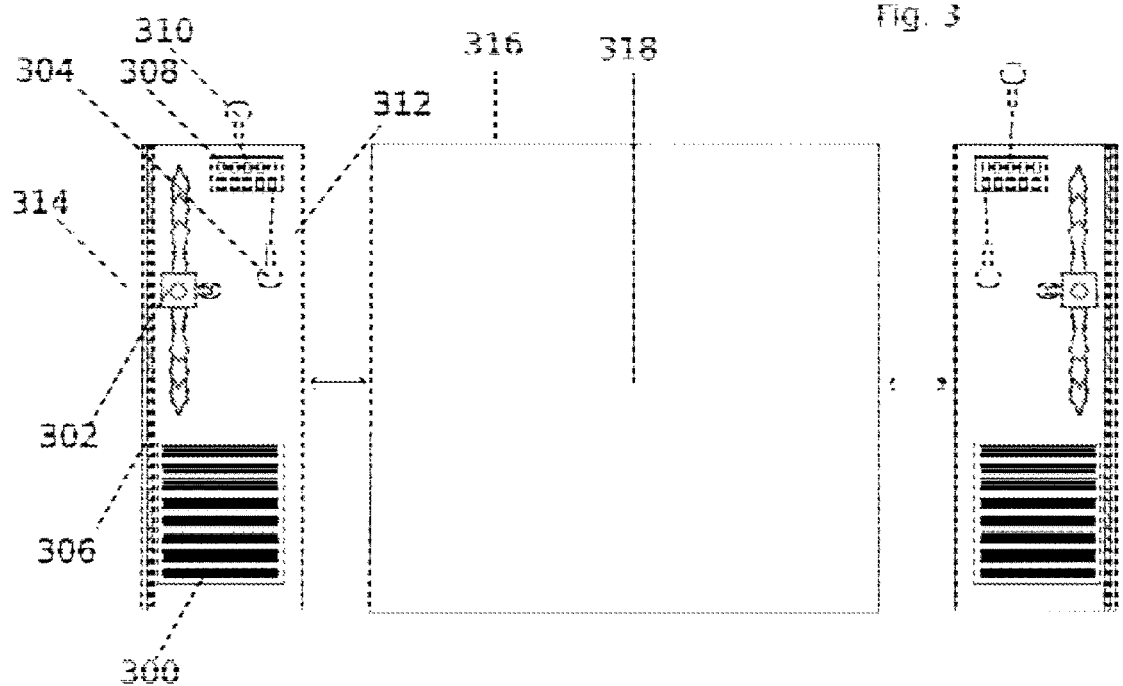
FIG. 3 shows the ventilation system, control system, and sorption system being disposed inside inlet and outlet doors.

In one variation, as shown in FIG. 3 the sorption system 300, ventilation system 302, pressure regulator 304, dust filter 306, control system 308, and sensor system 310 may be disposed within the interior 312 or on the surface of the inlet and/or outlet doors 314, with the doors being removably disposed in the sorption box 316. When the inlet and/or outlet doors are removed from the sorption box, the sorption box may be thereafter operate as simply an additional pipe or vent section in a larger HVAC system.

Figure 4:
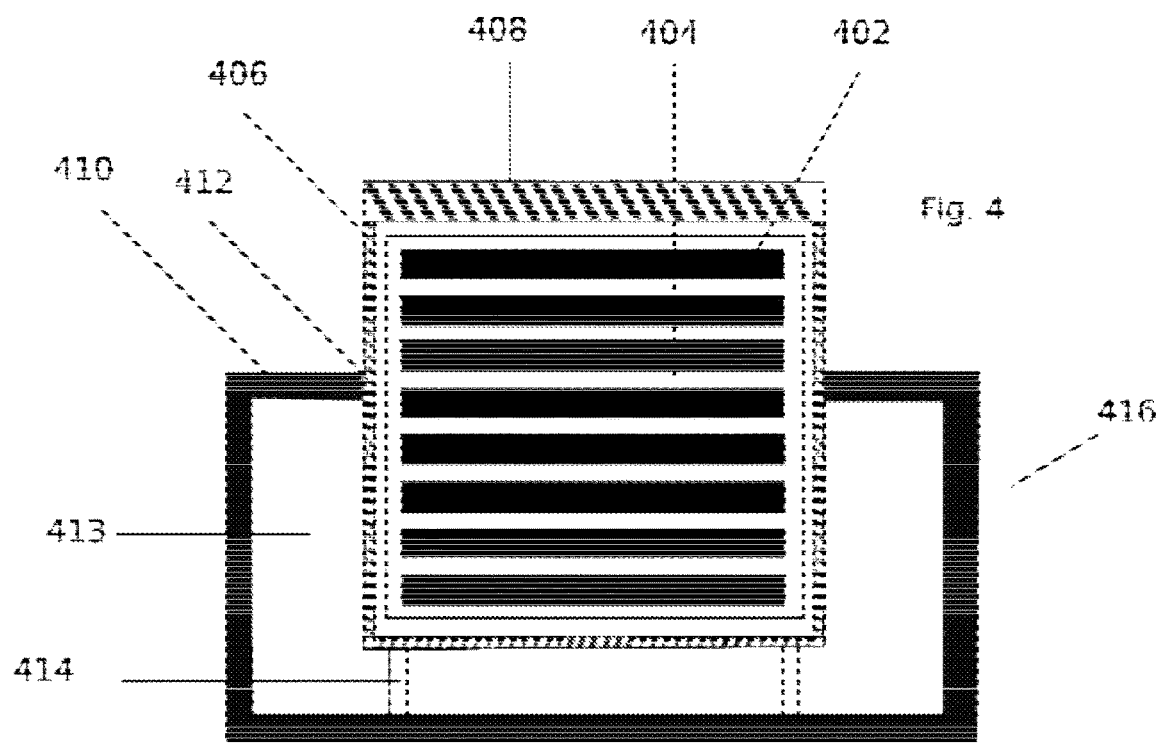
FIG. 4 shows sorption chambers and openings.

The sorption box may be configured to connect adaptably to tubing, piping, vents, or other HVAC components. The sorption box may be built into new HVAC systems or retrofitted into existing systems. It may be screwed or nailed in, or otherwise locked into place. The inlet and/or outlet walls may feature mechanisms, such as latch or screw-fit components, to adapt to the HVAC components. The sorption box may be positioned such that it is substantially or at least partly inside a building with the outlet wall positioned outside the building. Alternatively, the sorption box may be located inside a room in which filtering and adsorption is desired, or behind the wall of such a room but with access thereto. In one variation, the sorption box is independent of other HVAC components but is instead a stand-alone machine. As shown in FIG. 4, the sorption system may feature sorption units 402, the sorption units capable of adsorbing or absorbing flammable and/or toxic gases. The sorption units may be pads or packs made of or filled with sorption material. The sorption material may also be provided in coils, particularly meshed coils, thereby increasing the surface area of sorption. The sorption material may substantially fill the sorption box cavity, or, In order to facilitate replacement, the sorption units may be placed in and removed from sorption chambers 404, which are disposed inside the cavity. The chambers may hold the sorption units in place while still permitting airflow thereupon. A chamber may consist at least in part of a cage 406, which would enable air to enter while preventing a sorption unit from falling out. The cage may consist of wire or bars arranged latitudinally, longitudinally, diagonally, or in any other appropriate pattern. The cage may also comprise a mesh or floating screen.

The chambers may feature hatches 408 which provide access to the sorption units from outside the sorption box, but are also capable of being closed in order to prevent access thereof. The hatches may be substantially continuous and in line with the passage walls 410, being hingedly or slidably attached and engaged to the stationary portion of the passage walls.

In one variation, the sorption chambers themselves may be removable from the sorption box. The chambers may be fitted into chamber openings 412 that are disposed in the passage walls of the sorption box. The chambers and chamber openings may be screw-fit, constructed so that the former fits tightly into the latter, or otherwise configured to prevent the chambers from falling out of the chamber openings due to gravity or other unintended forces without grossly impeding a user from removing them. The chambers themselves may be disposed on a track 414 disposed inside the cavity and slidably removable from the sorption box 416.

Figure 5A:
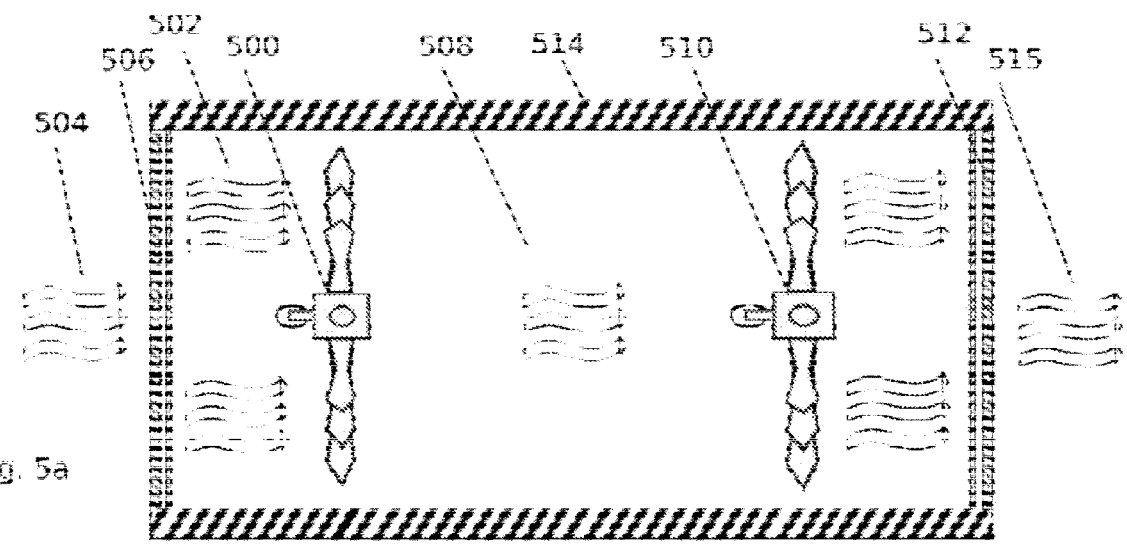
FIG. 5A-C show various fan configurations.
Figure 5B:
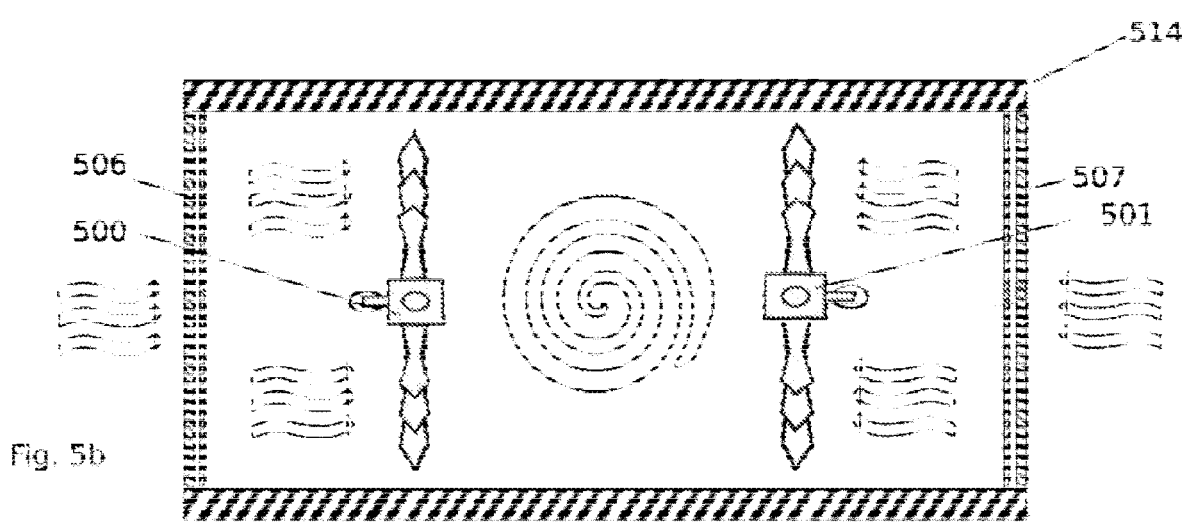

In one embodiment, the ventilation system may comprise an inlet fan and an outlet fan, with the inlet fan positioned close to the inlet wall and the outlet fan being positioned next to the outlet wall. The fans have a diameter approximating the sorption box diameter, so that all air entering the inlet wall may encounter and be handled by the inlet fan, and all air passing through the cavity may encounter and be handled by the outlet fan. As shown in FIG. 5A, the fans may be oriented so that the inlet fan 500 sucks in air 502 from the atmosphere 504 outside the inlet wall 506 and blows the air toward the cavity 508; conversely, the outlet fan 510 sucks in air from the cavity and blows the air toward and through the outlet wall 512 and out of the sorption box 515 However, in a preferred embodiment, as shown in FIG. 5B, the outlet fan operates as a second inlet fan, such that both fans suck air from the environment and blow air into the cavity. In this preferred embodiment, the sorption box 514 consists of a first and second inlet wall 506, 507 and a first and second inlet fan 500, 501, with the first inlet fan disposed behind the first inlet wall and the second inlet fan disposed behind the second inlet wall.

Figure 5C:
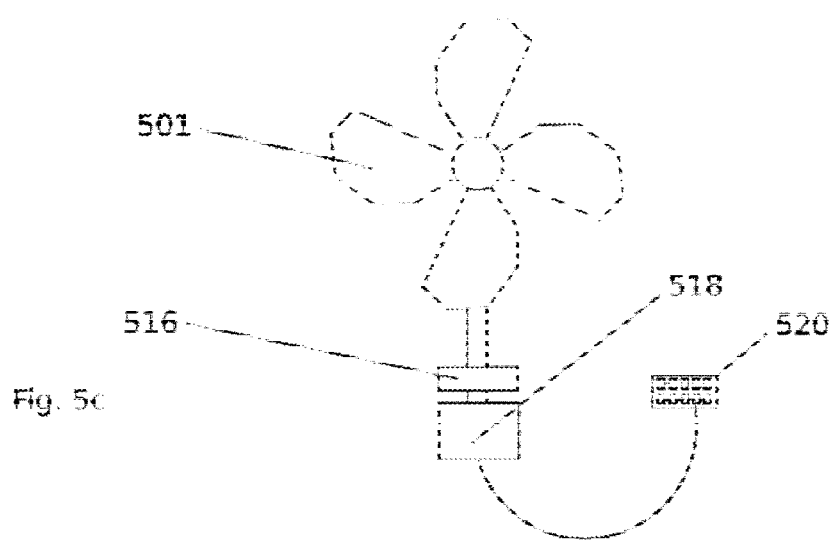

In the preferred embodiment described above, as shown in FIG. 5*c*, the second inlet fan may be disposed on a rotation mechanism 516, such as a rotating platform or a rotating axle, which enables the second inlet fan to rotate from a cavity-facing orientation to an atmosphere-facing orientation, thereby converting the sorption box from containment-type chamber to pass-through type. The rotating mechanism may be controlled manually by a user, such that the rotating mechanism may be physically rotated directly or indirectly by the user, or electrically. The rotating mechanism may be connected to a motor 518 which, when receiving a (wired or wireless) signal from the control system 520, a dedicated module, or a mobile device, will cause the rotating mechanism to rotate and thereby change the second inlet fan's orientation.

Figure 6:
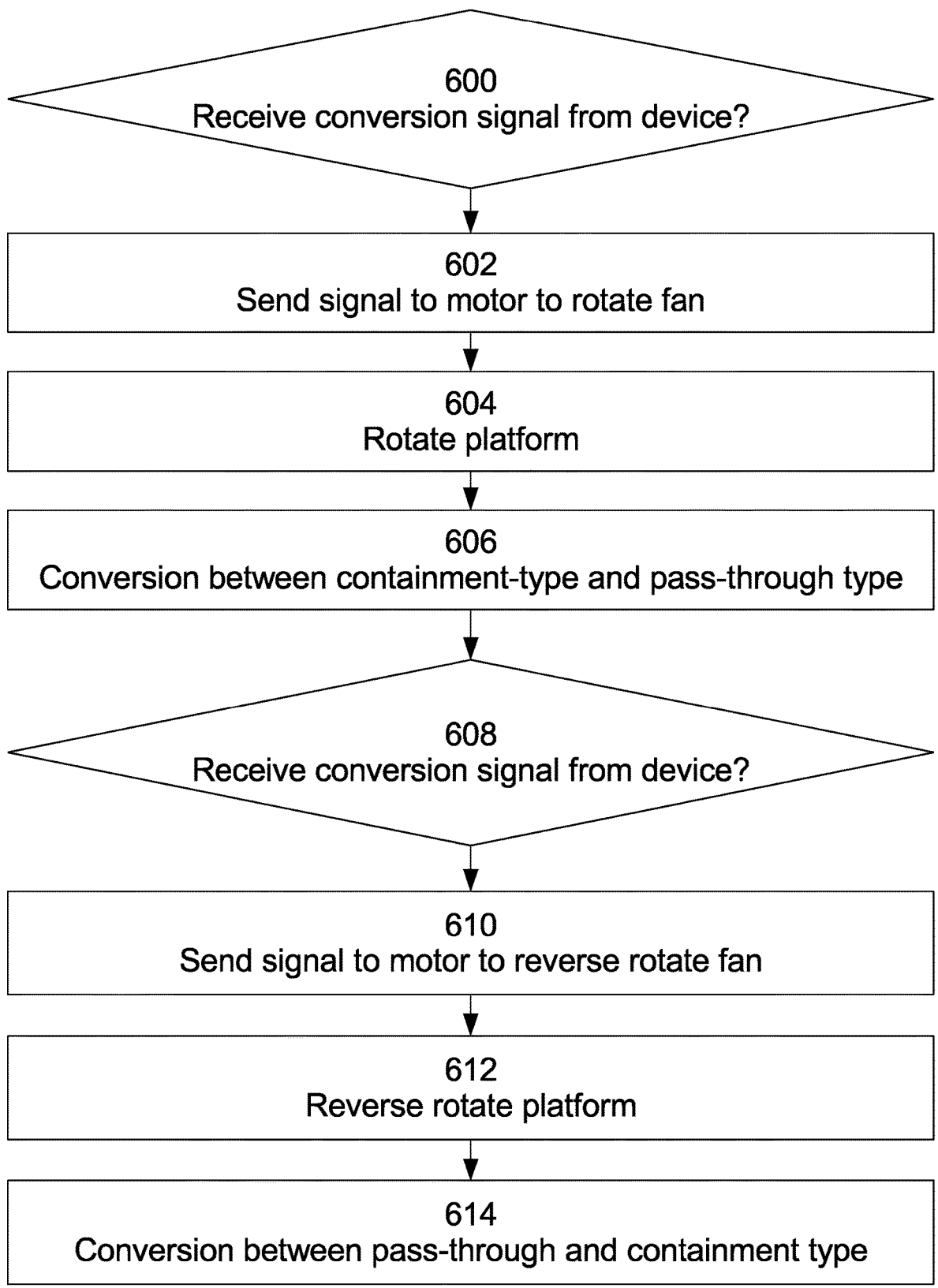
FIG. 6 is a flowchart showing conversions between fan configurations.

The conversion between containment-type and pass-through type, as shown in FIG. 6, may work as follows: The control system may receive a signal from a mobile device 600 to convert the containment-type chamber to a pass-through type chamber. The control system may send a signal to the motor to rotate the second inlet fan 602. The motor will then operate, causing the platform on which the second inlet fan resides to rotate 604. The inlet fan will then experience a full rotation (of approximately 180 degrees) 606, and conversion between the containment-type chamber and the pass-through type chamber will be achieved. If the control system receives a second signal from the mobile device 608 to convert the pass-through type chamber to a containment-type chamber, the control system will send a signal to the motor to reverse rotate the second inlet fan 610. The motor will then reverse rotate the second inlet fan 612 and the inlet fan will experience a full rotation 614, and conversion between the pass-through type chamber and the containment-type chamber will be achieved. Conversion may also be effected by reversing the spin direction of the fan(s).

The compressor may be disposed between the inlet fan and/or door and the cavity, and configured to reduce the volume of the gas in order to facilitate sorption by the sorption units.

The gas collection container may be rigid or made of inflatable material. It is preferably in fluid communication with the cavity, thereby leeching densified and contaminated air from the sorption box. This gas collection container may, in one variation, be intermediated by a ventilation fan in order to accelerate gas collection.

Transport of contaminated or cleaned air may be facilitated by a series of valves intermediating the various components of the device. For example, a first set of valves may control flow from the compressor to the cavity, a second set of valves may control flow from the cavity to the gas collection container, and a third set of valves may control flow from the cavity to outlet fans or to the outlet wall.

The dust filter is (dust filters are) preferably disposed within or behind the inlet wall(s). The dust filter is configured to catch particles smaller than 1 mm in diameter which the inlet wall(s) otherwise might not catch, such as dust particles, which are between 2.5 and 10 microns.

Figure 7A:
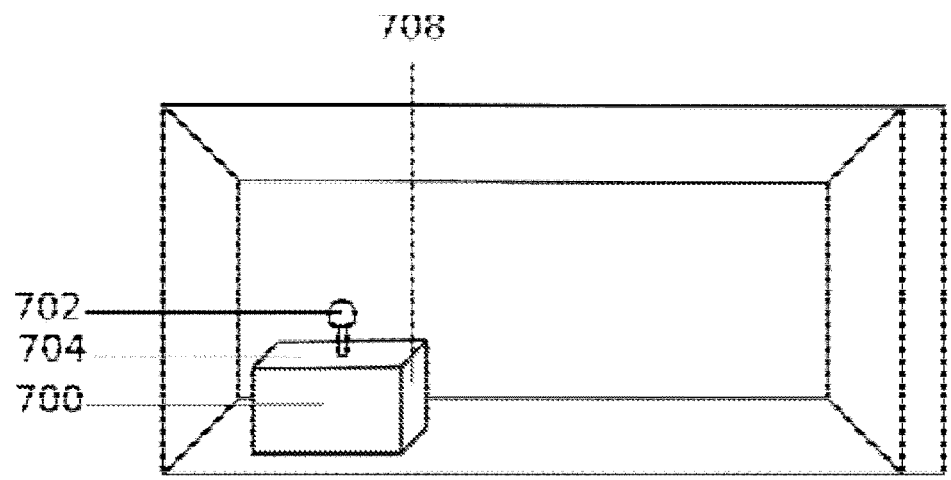
FIG. 7A-C shows the sensor system.
Figure 7B:
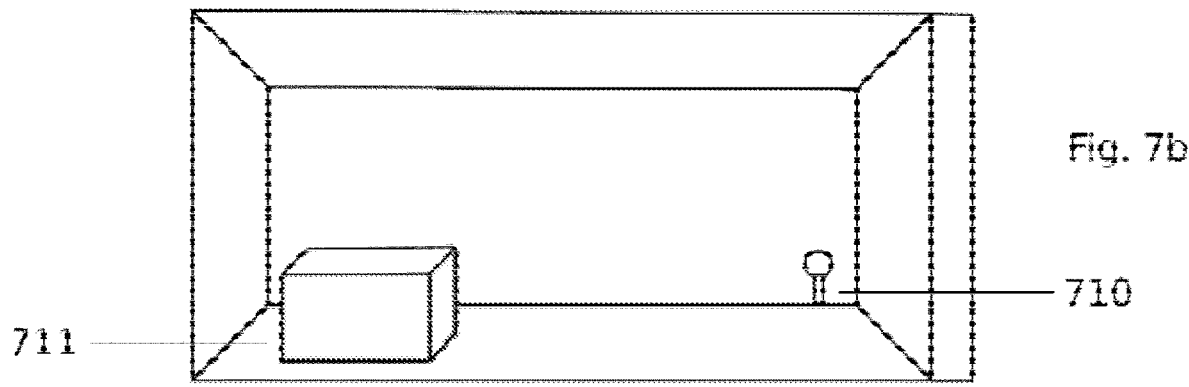
Figure 7C:
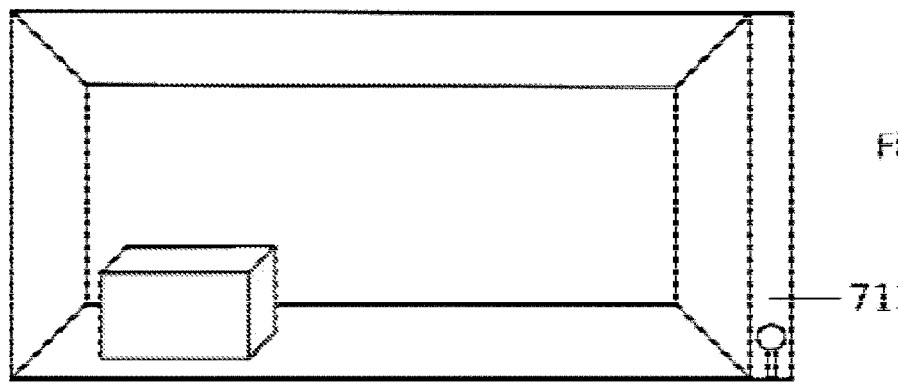

As shown in FIGS. 7A-C, the sensor system 702 may be positioned anywhere on the sorption box 700, such as the passage 704, inlet or outlet walls 708, or elsewhere, such as in one part of a room 710 while the sorption box is located in another part of the room 711 or even within a wall 712. If the sensor system is not physically attached to the sorption box, it may be connected via wires or engaged to the control system via a wireless interface, such as bluetooth or WiFi.

The sensor system may include a gas sensor configured to detect flammable or toxic gases. Examples of gas sensors include metal oxide based gas sensor, optical gas sensor, electrochemical gas sensor, capacitance-based gas sensor, calorimetric gas sensor, or acoustic based gas sensor. The gas sensor may consist of sensing elements such as a gas sensing layer, a heater coil, an electrode line, a tubular ceramic, or an electrode. Examples of gases which may be sensed include methane, butane, LPG, smoke, alcohol, ethanol, CNG gas, natural gas, carbon monoxide, carbon dioxide, nitrogen oxides, chlorine, hydrogen gas, ozone, hydrogen sulfide, ammonia, benzene, toluene, propane, formaldehyde, and other various toxic or flammable gases.

Figure 8:
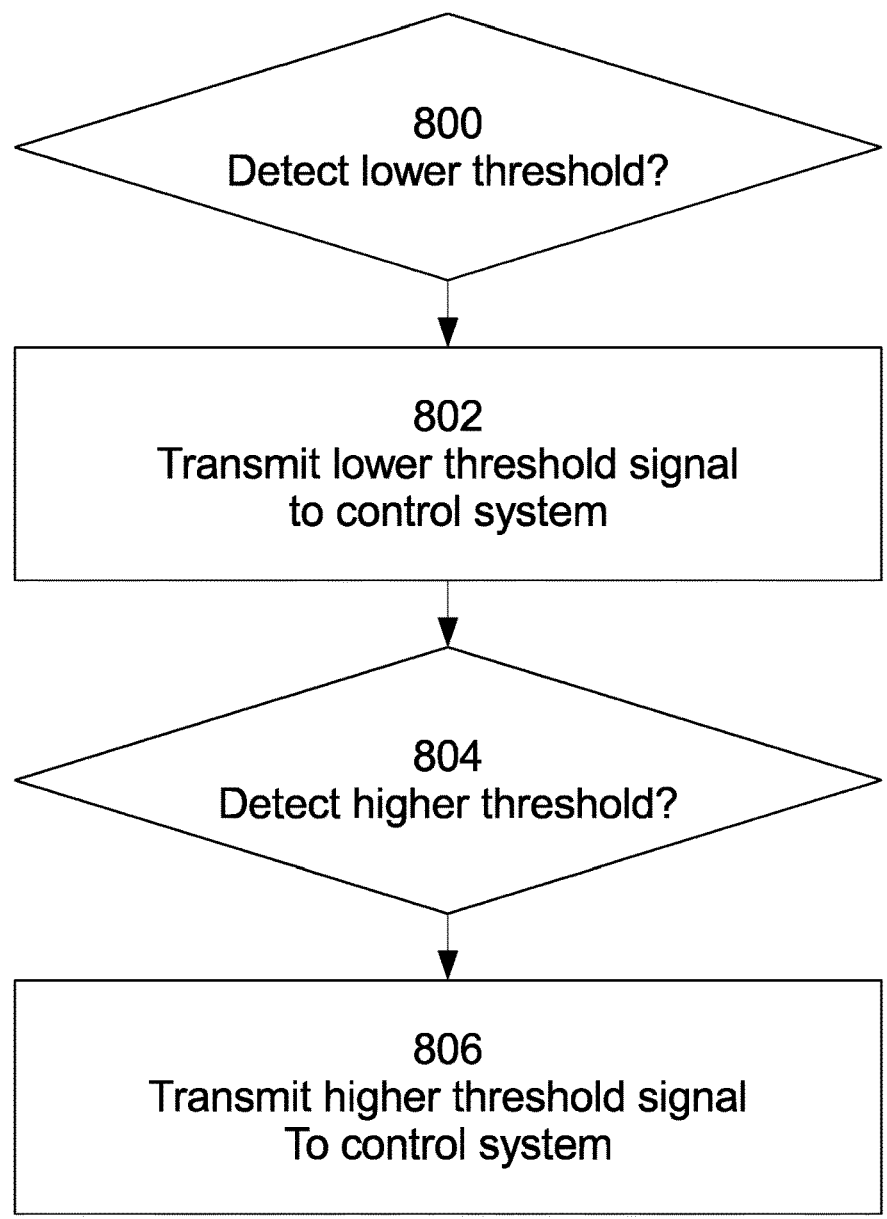
FIGS. 8-9 are flowcharts showing system processes.

Upon detecting a designated concentration level of an undesirable gas, the sensor system is configured to transmit a gas detection signal to a wireless receiver inside the control system. The designated concentration levels of undesirable gases may be based on lower flammability limits or on recognized toxicity levels, which are levels where the gas becomes dangerous to human or animal health. In one variation, as shown in FIG. 8, there are two separate gas detection levels—a lower threshold and an upper threshold. In this variation, the sensor system transmits a lower threshold gas detection signal to the wireless receiver 802 upon detecting a lower threshold of gas 800, which is a level which it is considered advisable to human operators or users but which does not yet reach or approach the lower flammability limits or recognized toxicity levels, and transmits an upper threshold 806 gas detection signal upon detecting an upper threshold of gas 804.

The sensor system may be configured to detect the concentration of a given gas, approximate that concentration numerically, and transmit the numerical concentration to the control system or directly to a visual display to enable users or operators to view and track the gas levels. The concentration levels may be captured and transmitted in real time, or captured at reoccurring intervals, such as once an hour, once a day, or once a week. The captured concentration levels may be saved in a database for future reference. In one variation, the concentration levels are transmitted to a dedicated module or mobile device, where they are converted into trending data, and the trending data may be saved on the module or device and displayed upon request by the user.

Figure 9:
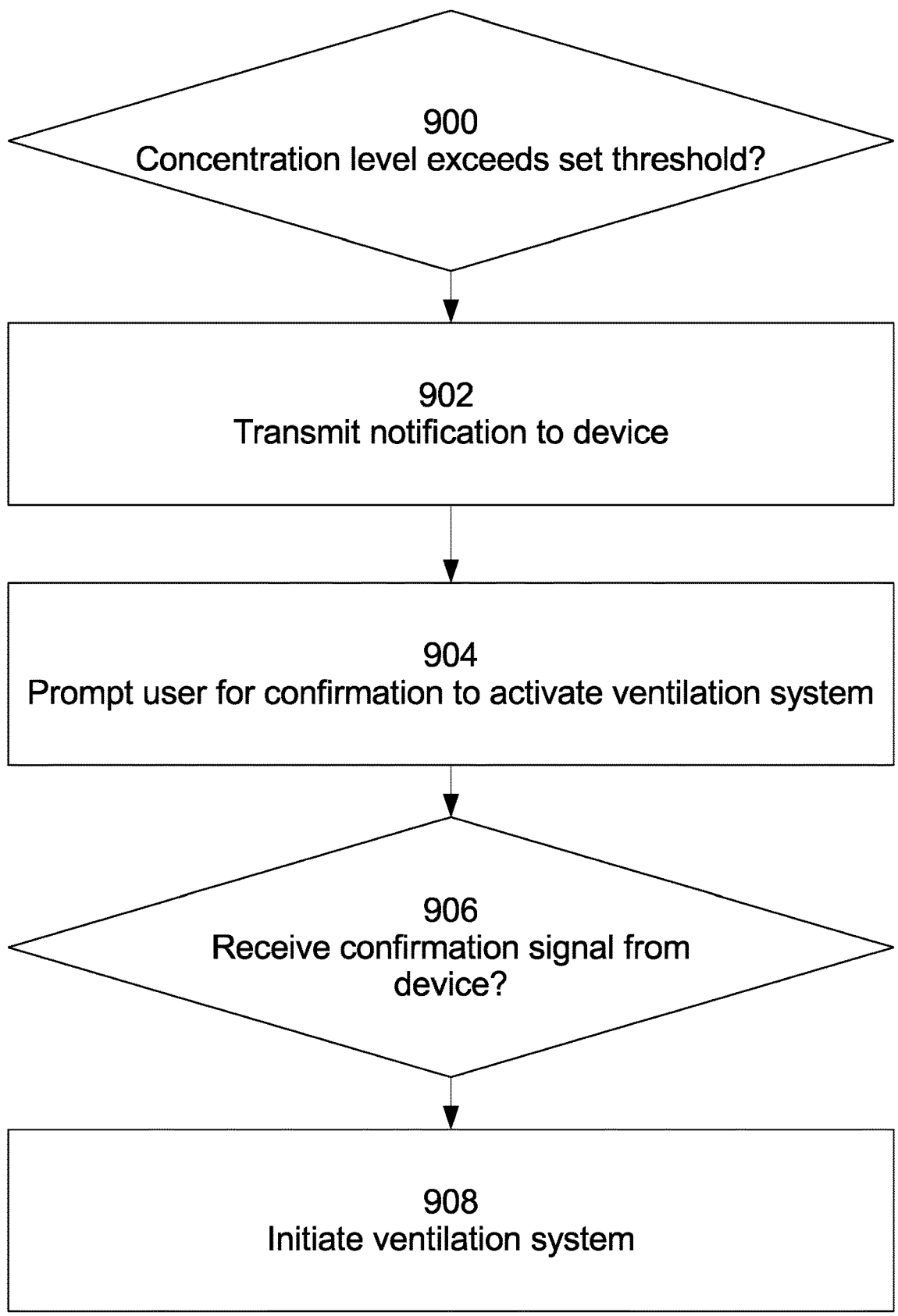

As shown in FIG. 9, upon capturing a concentration level that equals or exceeds a set threshold 900, the sensor system may transmit a notification wirelessly to the user's mobile device or a dedicated module 902, informing the user of the concentration level or that the concentration level has exceeded the set threshold, and then prompt the user for confirmation to activate the ventilation system 904. In one version, the ventilation system is automatically activated without requiring user confirmation.

The control system comprises a set of processors and wireless receivers disposed within a container. Upon receiving the wireless detection signal from the mobile device 906, the control system is configured to initiate or permit an electric flow to the ventilation system 908, thereby turning on the fans. In the variation described above, the control system may permit electric flow to the ventilation system upon receiving an upper threshold gas detection signal, but only turn on a warning signal upon receiving a lower threshold gas detection signal. The warning signal may be a light, such as a bulb, LED, or other illumination component, configured to illuminate in either a steady stream or flashing pattern, and which is signalled electrically or wirelessly by the control system. The warning signal may be a text message or other notification sent to a human user or operator's phone or a separate display screen. The warning signal may also be an audio transmission, such as a beeping sound, emitted from a speaker disposed on or in the sorption box or else positioned in the targeted room and wirelessly connected to the control system. An exemplary manifestation of the control system may be a SCADA (supervisory control and data acquisition) system, which includes software and hardware elements enabling the control of processes locally or remotely, the monitoring, gathering, and processing of real-time data, interaction with devices such as sensors, valves, pumps, and motors though a human-machine interface, and the recording of events into a log file.

In one variation, the user may communicate with the control system and/or sensor system using the dedicated module or mobile device via a dedicated user interface. The user may observe the concentration levels in real time and observe historical concentration data. The user may send a signal to the control system to turn on the fan system based on target concentration levels, which may be set by the user using the user interface, and/or manually.

The control system and/or the ventilation system may be mechanically, hydraulically, or battery operated, feature a plug for inserting into an electrical outlet, and/or hardwired into a building's electrical wiring. If the control system is battery operated, the battery may be contained in a battery box, with the battery box being disposed inside or adjacent to the control system. The battery box may be positioned so that it is accessible from outside the sorption box so that the battery may be easily removed and replaced. The battery box may feature a port which passes through the walls of the sorption box and configured to receive a battery charger.

The control system may impose various activity programs on the components of the device, principally by controlling the electrical flow to the one or more fans and the one or more motors, thereby turning the one or more fans on or off, increasing or decreasing rotations speeds of the one or more fans, or switching the directional orientation between the outlet orientation and the inlet orientation. The control system may also control the valves that permit or block fluid flow from entering the device, moving throughout the device, (such as between the compressor and the cavity, the cavity and the gas collection container, the cavity and the outlet fans), and exiting the device. The doors comprise a row of shutters, such that when the shutters are oriented perpendicular to a door, the door is in an open state, and when the shutters are oriented substantially in line with the door, the door is in a closed state. The shutters may be electrically and mechanically controlled by the control system as well.

In one program, the control system determines if the sorption units have reached capacity based on the internal contaminant gas signals, and if so, imposes a containment program on the ventilation system, with the containment program featuring either all of the one or more fans turned off or turned on and put into the inlet orientation. The containment program may be subceeded by a collection program, in which the valves connecting the cavity to the gas collection containers are opened for a span of time, ideally until the gas collection containers are filled to capacity, hereafter the valves are shut off. To assist in determining whether the gas collection containers are filled to capacity, a pressure sensor in signal communication with the control system may be disposed between the valve and the gas collection container. This gas collection container may be removably attached to the cavity such that once it is removed, it may be sealed up. In one variation, the valve is principally attached to the gas collection container and is removed with it. In another variation, the valve is principally attached to the cavity, and the gas collection container must be sealed by other means, such as via a cap or a separate valve.

In another program, the control system determines if the contaminant gas levels in the atmosphere are too high (although this may also be the default assumption for the control system, and therefore a default program). If so, the control system imposes a concentration program on the ventilation system, with the concentration program set for increasing the speed of the one or more fans in an inlet orientation or switching one or more fans from an outlet orientation to an inlet orientation.

In yet another program, the control system determines if the sorption box pressure is too high, and if so, imposes a pass-through program on the ventilation system, with the pass-through program featuring at least one fan in an outlet orientation.

Figure 10:
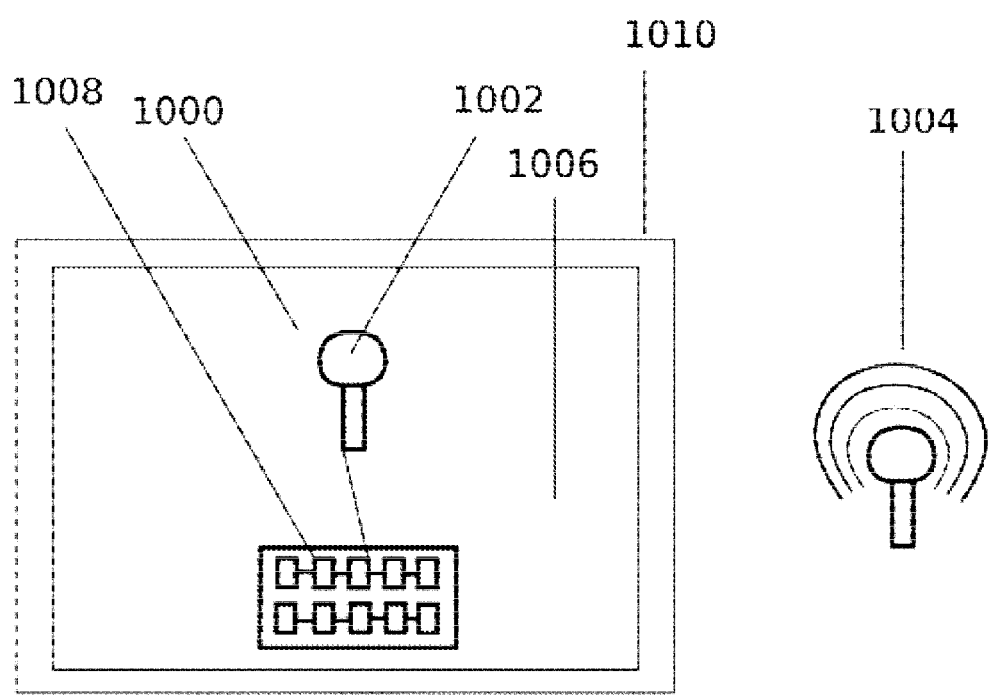
FIG. 10 shows sensor system configurations.
Figure 11:
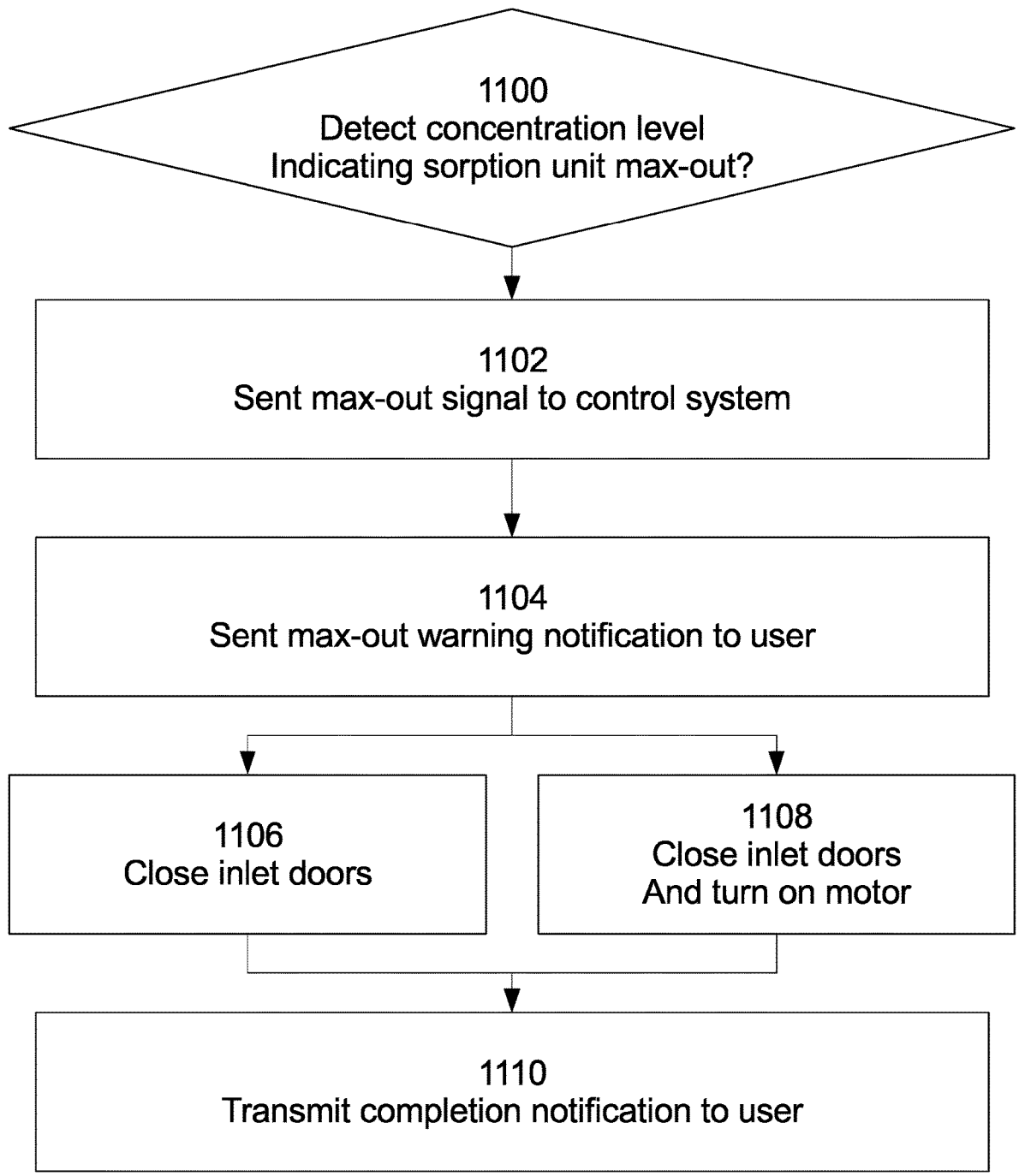
FIG. 11-13 are flowcharts showing system processes.

In one variation, as shown in FIG. 10, the sensory system 1000 comprises a first 1002 and second sensory set 1004, with the first sensory set being positioned inside the cavity 1006 and being electrically connected to the control system 1008 and the second sensory set being positions outside the sorption box 1010, perhaps several to many feet away, and connected to the control system using a wireless protocol. This first sensory set may also be in wireless communication with the user's mobile device or dedicated module, and may inform the user when the concentration level of gas in the sorption box is such that the sorption units may have reached their sorption limits, thereby informing the user that the sorption units may need to be checked or replaced. This information may also influence the user, and additional information may be sent suggesting, to close the inlet (and outlet doors), to thereby keep the gas from escaping the sorption box and thereafter turn off the ventilation system, or to rotate the second inlet fan into an outlet fan in order to blow the gas out of the sorption box and into collection bags or an atmosphere outside the building (or into a collecting pipe or apparatus). These steps may also be automated according to the following process, as shown in FIG. 11: 1. The second sensory set detects a concentration level which indicates that the sorption capacity of the sorption units have maxed out 1100. 2. The control system receives this signal 1102, and then wirelessly transmits a notification to the user 1104. 3a. The control system may trigger the inlet doors to close, and thereby prevent the gas from deadsorbing or deabsorbing and exiting the sorption box 1106, or 3b. The control system may trigger the first inlet door to close and trigger the motor connected to the second inlet fan to rotate into an outlet fan and blow the lingering gases into a collection bag, pipe, or apparatus or into the atmosphere 1108. 4. Transmit a process completion signal to the user 1110.

Figure 12:
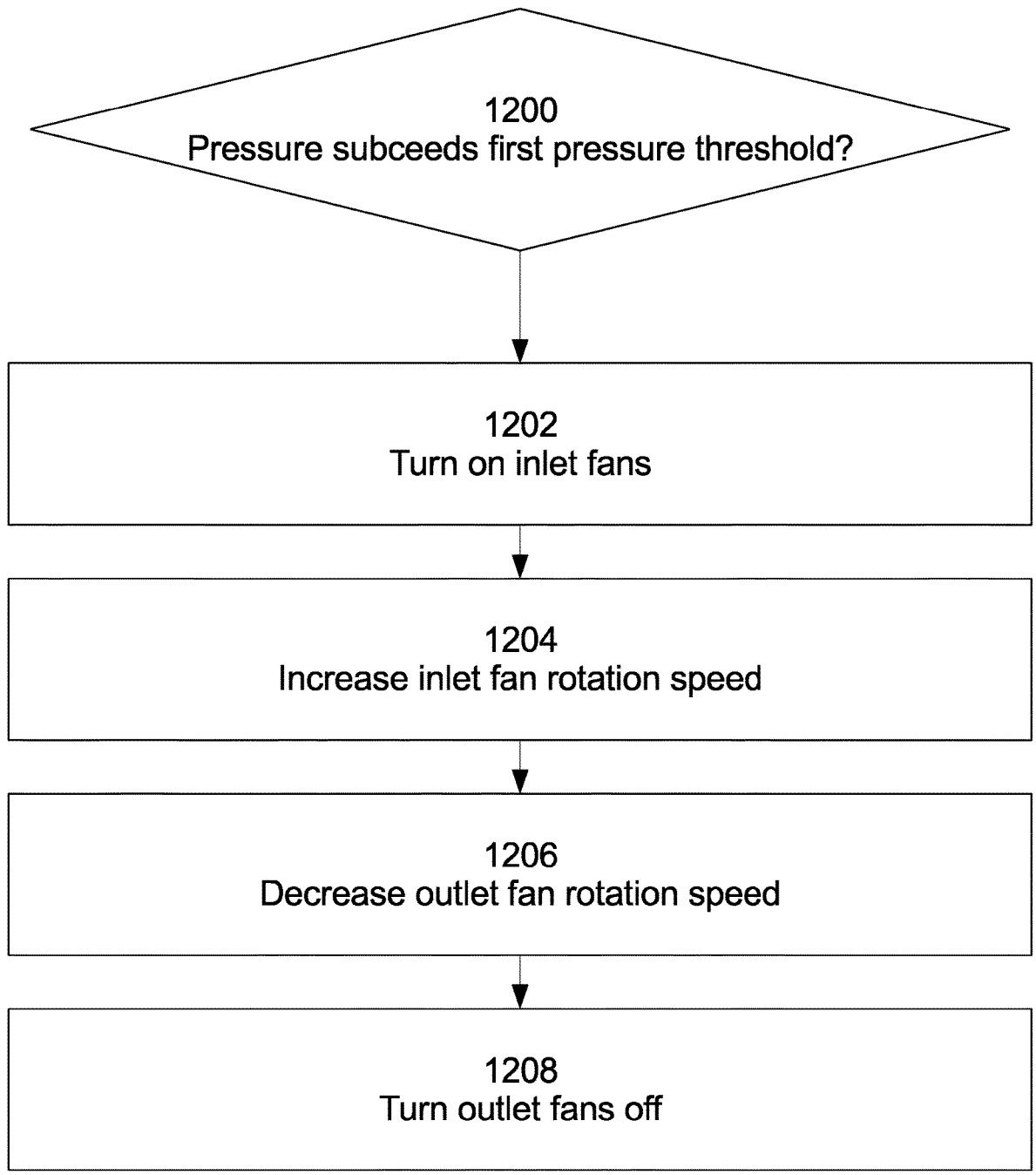
Figure 13:
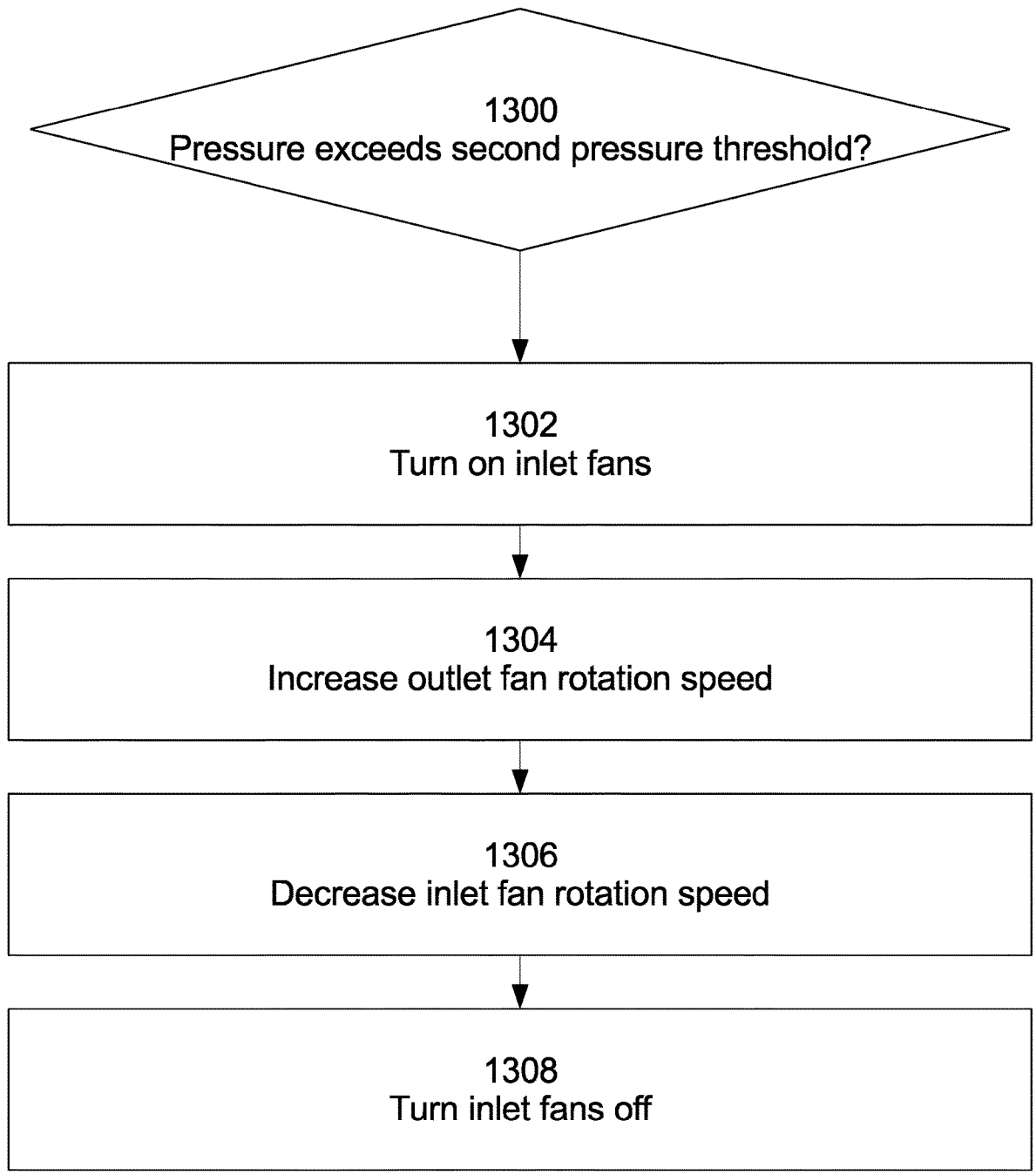

The pressure regulator features a pressure sensor designed to detect the measurement of gas pressure. Based on the degree of pressure imposed on the sensor, the pressure regulator generates an electrical signal to convey the pressure measurement to other components. As shown in FIG. 12, while the pressure subceeds a first pressure threshold 1200, the pressure regulator may communicate with the ventilation system to turn the input fan(s) on 1202, permit or instruct the input fan(s) to increase their rotation speed 1204, turn the output fan(s) off 1206, and/or permit or instruct the output fan(s) to decrease their rotation speed 1208, thereby increasing the density of air, and thus the pressure, in the adsorption box. Conversely, as shown in FIG. 13, when the pressure exceeds a second pressure threshold 1300, the pressure regulator may communicate with the ventilation system to turn the output fan(s) on 1302, permit or instruct the output fan(s) to increase their rotation speed 1304, turn the input fan(s) off 1306, and/or permit or instruct the input fan(s) to decrease their rotation speed 1308, thereby decreasing the density of air, and thus the pressure, in the adsorption box.

As shown in FIG. 14, a plurality of sorption boxes may be positioned in a series 1400, such that once the sorption capacity of the sorption units of a first sorption box are maxed out, the first sorption box may blow its gas-heavy air into the second sorption box, and so on. A plurality of sorption boxes may simultaneously 1402 or alternately 1404 be positioned in parallel, such that each sorption box has an inlet adjacent to the atmosphere and not to the outlet of any other sorption box. Each sorption box may be dedicated to capturing a different type or category of gas; for example, a first set of sorption boxes may be dedicated and configured to capturing flammable gasses while a second set of sorption boxes may be dedicated and configured to capturing toxic gasses. Each sorption box of the first set may be dedicated to a subset of flammable gasses and each sorption box of the second set may be dedicated to a subset of toxic gasses.

The sorption box may be sized proportional to the space in which filtering and gas sorption is sought, and may be calculated according to the equations shown in FIG. 15.

Additional examples of sorbents include catalytic sorbents, photocatalysts, polymerics, MOFS, Alkali metals such as carbonates and oxides, amine solid sorbents, carbonaceous materials such as carbon nanotubes and carbon molecular sieves, zeolites, mesoporous silica, alumina, hydrotalcite-like compounds (HTICs), metal-based oxides such as CaO based sorbents, porous MgO, Sodium Zirconate, Lithium compounds, and $Na_2O$ promoted alumina, activated carbons, sorbents. So-called photocatalysts, such as titanium dioxide, work to disinfect by, upon being disposed to light, generate hydroxyl radicals.

Figure 18:
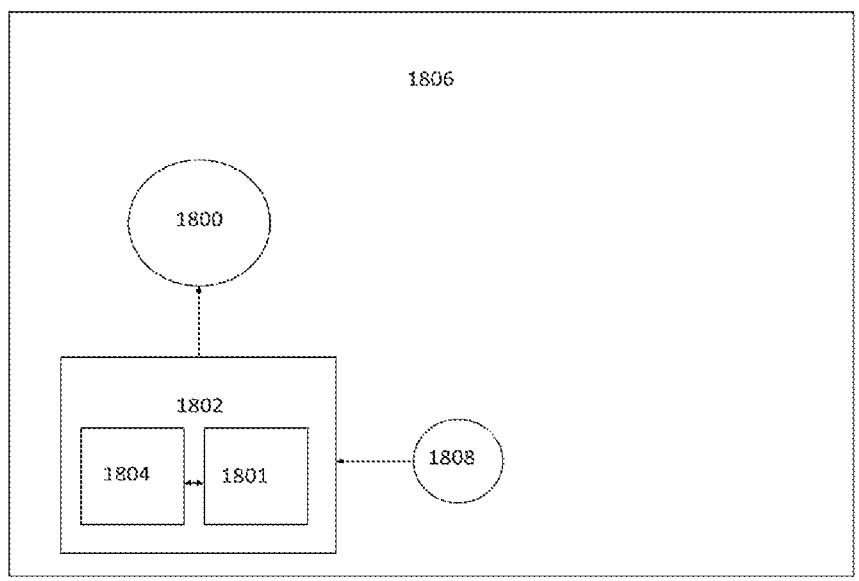
FIG. 18 shows a sorption unit coupled to an ultra violet light emitter.

In one embodiment, one or more sorbents and/or the sorption box are coated with crystalline coating material, which is configured to generated hydroxyl radicals upon being exposed to light. Hydroxyl radicals are observed to denature viruses, such as SARS-Coronavirus, by damaging viral exterior features, such as the crown or spike proteins, puncturing the lipid membrane, and exposing the RNA contents. The crystalline coating material may include metal organic frameworks (MOF), which operate as desiccants by providing an enlarged, porous, surface area with external-facing molecules in a cage-like structure that are likely to bind and thereby capture free-floating molecules. The crystalline coating material may be added to traditional sorbents as an applied layer or may be used as sorbents by themselves. The use of crystalline coating material in conjunction with other sorbents and/or the sorption box may also provide disinfecting effects on bacterial and fungal growth. In another embodiment, the sorption box is coupled with an Ultra Violet (UV) emitting bulb or light source. The use of UV is an effective method of denaturing viruses, and acts to damage the exterior features of the virus, thereby exposing and further damaging the RNA contents. As shown in FIG. 18, the UV light source 1800 may be connected electrically and informationally to the sorption box control system 1801 of the sorption box 1802 in order to enable automatic or manual control over the duration, intensity, and wavelength of the UV light. The control system may set the UV light settings based on feedback from the sensor system 1804, which may detect the number of individuals inside a room 1806 using infrared sensors 1808, and whether individuals sneeze or cough using microphones or other sound sensors. In a more advanced feature, the sensor system includes a swab arm that mechanically ushers potential viral matter that has settled on a surface interior or exterior to the sorption box, depending on the sensor setup, into a miniaturized PCR (polymerase chain reaction) or LFT (lateral flow test) testing system, which may include a thermocycler, immunoassay technology using nitrocellulose membranes, colored nanoparticles or labels, and antibodies. After running a PCR or LFT test, the control system can be informed whether viral matter is present, as well as the specific type of viral matter, and run the UV light parameters according to the specific parameters determined to most capably destroy the viral matter.

In one embodiment, the sorption box features a heating mechanism, such as conventional heating elements found in portable heaters, and which are electrically connected to the control system. The control system may provide for manual control over heating, automatic control based on feedback provided by thermometrical sensors, or a combination of the two, such that a user can program the heating elements to activate upon the detection of a lower threshold temperature and deactivate upon the detection of a higher threshold temperature. The user may also program the control system to activate the heating elements based on sorbent activation requirements. The heating system may also be used for humidity control in order to maintain the efficacy of the sorption units. Dehumidification may be scheduled or programmed to occur upon the detection of a set humidity threshold. Finally, the control system may be configured to apply a desorption program upon detecting an adsorption saturation point has been reached or based on a schedule.

In one embodiment, the sorption units may feature a multi-sorbent complex, featuring multiple layers stacked together, with each layer comprising a different material, thickness, density, or configuration of sorbents. The layers may be stacked in a pile, or radially such that a first layer comprises a core which is then surrounded nearly entirely by a second layer, and so on.

Figure 16:
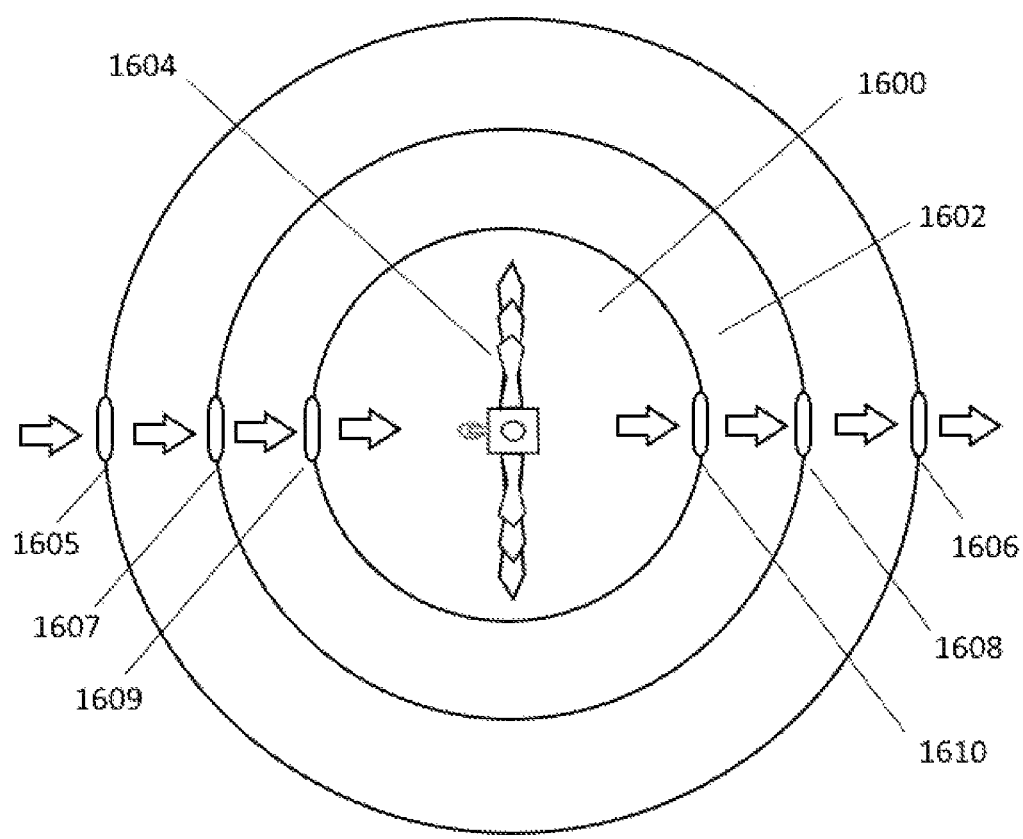
FIG. 16 shows sorption units stacked cylindrically.
Figure 17:
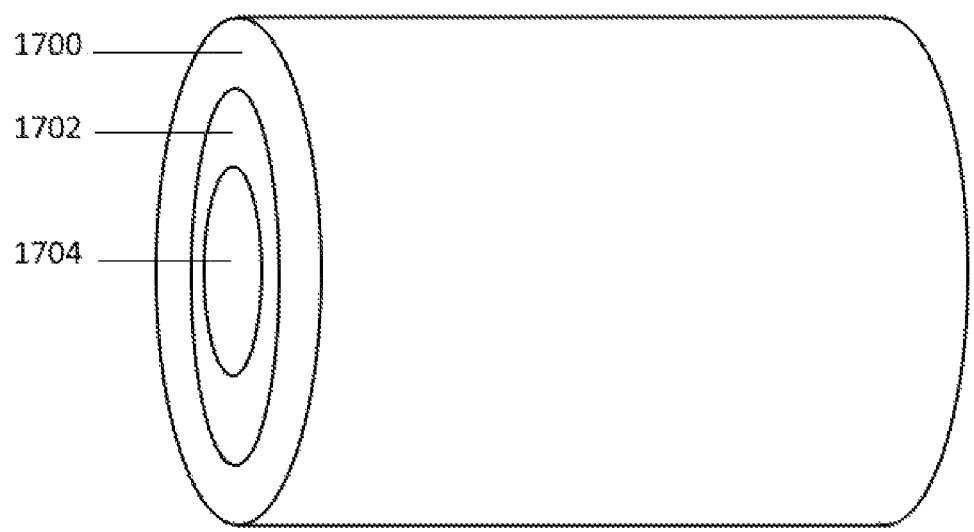
FIG. 17 shows sorption units stacked cylindrically.

In another embodiment as shown in FIG. 16-17, the sorption boxes may be shaped cylindrically and sized so that one sorption box 1600 may be placed internally to a second sorption box 1602 as an internal cylindrical layer. Each sorption box may have its own dedicated ventilation system so that the sorption boxes may be separated and used independently. In one variation, they may share the mechanical aspects of a single ventilation system 1604 placed in a "core" or inner-most layer and/or the outer-most layer. The ingresses 1605, 1607, 1609 and egresses 1606, 1608, 1610 of the sorption boxes may line up so as to enable the atmosphere to flow through (and be sucked in via the ventilation system) the outer-most layer to the inner-most layer. As shown in FIG. 17, the ingresses 1700, 1701, 1703 and egresses (not shown) may also be disposed on the exposed face of all layers so that ingress and egress of atmospheric air may occur directly through each layer without having to first pass through a separate layer. As mentioned previously, each sorption unit may be dedicated to a specific type of gas control and may be activated independently based on the detection of its target gas/contaminant (i.e., dust, pollen, smoke, viral particle, toxic gas, flammable gas, etc.). Thus, a first sorption unit may target toxic gasses, a second sorption unit may target combustible gasses, a third sorption unit may target viral, bacterial, or fungal particles, and a fourth sorption unit may target air purification.

As previously discussed, the control system may transmit a communication to a user's mobile device or to a dedicated device conveying sorption system activity, including instructions to replace one or more sorption units. The control system may also be configured to transmit communications to third parties such as fire departments. The transmission may be wirelessly via Bluetooth, WiFi, or some other wireless protocol. In one embodiment, each sorption box and/or sorption unit is equipped with a scale or other weight measuring mechanism to determine when the sorption unit has reached its saturation point. The system may also make this determination based on measurements of inlet flowrate and/or concentration. The system may also include a user interface configured to inform the user as to the location of sorption unit disposal or recycling services. Such information may be displayed as pins on a map. The system may either itself comprise or be coupled to a GPS application.

The invention claimed is:

1. A disinfectant and accumulation control device comprising a first sorption box, a second sorption box, a sorption system, a ventilation system, a sensor system, a pressure regulator, and a control system; the ventilation system being in electrical communication with the control system, the control system being in informational communication with the sensor system and the pressure regulator; the first and second sorption boxes being enclosures against an atmosphere surrounding the sorption boxes and comprising: one or more passage walls, pass-through walls, and a cavity, the cavity surrounded by the one or more passage walls and the pass-through walls, the pass-through walls configured to permit air between the cavity and atmosphere; the one or more passage walls spanning a first of the pass-through walls to a second of the one pass-through walls; the sorption system comprising a first sorption unit and a second sorption unit, the first sorption unit made of a material capable of adsorbing or absorbing flammable or toxic gases and the second sorption unit made of a material capable of destroying viral particles, with the first sorption unit disposed in the first sorption box and the second sorption unit disposed in the second sorption box; the sensor system comprising one or more gas sensors configured to detect flammable or toxic gases and transmit gas detection signals to the control system and one or more viral particle sensors configured to detect the viral particles and transmit the viral detection signals to the control system; the ventilation system comprising one or more fans, the one or more fans positioned adjacently to the pass-through walls and oriented so that that they suck air through or toward the pass-through walls; the control system comprising a processor programmed to receive the gas detection signals and the viral detection signals from the sensor system, control the one or more fans based on the gas detection signals by turning the one or more fans on or off, or increasing or decreasing rotation speeds, and control an ultraviolet light emitting element based on the viral detection signals by turning the ultraviolet light emitting element on or off, setting a radiation intensity of the ultraviolet light emitting element, and setting a radiation duration of the ultraviolet light emitting element; the first sorption box having an outer diameter or width and the second sorption box having an inner diameter or width, with the outer diameter or width of the first sorption box being equal to or less than the inner diameter or width of the second sorption box; with the sorption boxes disposed in a substantially layered configuration such that the first sorption box is disposed within the second sorption box and the second sorption box fits around the first sorption box.

2. A disinfectant control device comprising a sorption box, a sorption system, a ventilation system, a sensor system, a pressure regulator, and a control system; the ventilation system being in electrical communication with the control system, the control system being in informational communication with the sensor system and the pressure regulator; the sorption box being an enclosure against an atmosphere surrounding the sorption box and comprising: one or more passage walls; pass-through walls, and a cavity, the cavity surrounded by the one or more passage walls and the pass-through walls, the pass-through walls configured to permit air between the cavity and atmosphere; the one or more passage walls spanning a first of the pass-through walls to a second of the pass-through walls; the sorption system comprising sorption units, the sorption units made of material capable of destroying viral particles; the sensor system comprising one or more viral sensors configured to detect the viral particles and transmit the viral detection signals to the control system; the ventilation system comprising one or more fans, the one or more fans positioned adjacently to the pass-through walls and oriented so that that they suck air through or toward the pass-through walls; the control system comprising a processor programmed to receive the viral detection signals from the sensor system, and control the one or more fans based on the viral detection signals by turning the one or more fans on or off, or increasing or decreasing rotation speeds.

3. The device in claim 2, the sorption units made of metal organic frameworks.

4. The device in claim 2, the sorption units having a crystalline coating.

5. The device in claim 3, with the material capable of destroying the viral particles coated with crystalline coating, with the crystalline coating configured to release hydroxyl radicals upon being exposed to light.

6. The device in claim 2, also comprising an ultraviolet light emitting element.

7. The device in claim 6, the processor programmed to control the ultraviolet light emitting element based on the viral detection signals by turning the ultraviolet light emitting element on or off.

8. The device in claim 7, the processor programmed to control the ultraviolet light emitting element based on the viral detection signals by setting a radiation intensity of the ultraviolet light emitting element.

9. The device in claim 7, the processor programmed to control the ultraviolet light emitting element based on the viral detection signals by setting a radiation duration of the ultraviolet light emitting element.

10. The device in claim 2, the material capable of destroying the viral particles comprising a first layer and a second layer, with the first layer configured to damage viral particles of a first type and the second layer configured to damage viral particles of a second type.

11. The device in claim 10, with the first and second layers being layered radially forming an inner core layer and an outer external layer.

12. The device in claim 6, the sensor system comprising infrared detection sensors configured to detect the number of individuals proximate to the device, encode the number of individuals proximate to the device as proximate individual data, and transmit proximate individual data to the control system, with the processor programmed to control the ultraviolet light emitting element based on the proximate individual data.

13. The device in claim 6, the sensor system comprising sound sensors configured to detect coughing or sneezing sounds, encode the detection of coughing or sneezing sounds as possible infection data, and transmit the possible infection data to the control system, with the processor programmed to control the ultraviolet light emitting element based on the possible infection data.

14. The device in claim 6, the sensor system includes a PCR or LFT testing system which is encoded to operate based upon the viral detection signals.

15. The device in claim 14, with the viral detection signals including a viral type detection.

16. The device in claim 2, the control system configured to send viral detection data to a mobile device.

17. A disinfectant control device comprising a sorption box, a sorption system, an ultraviolet light emitting element, a sensor system, and a control system; the control system being in informational communication with the sensor system and electrical communication with the ultraviolet light emitting element; the sorption box being an enclosure against an atmosphere surrounding the sorption box; the sorption system comprising sorption units, the sorption units made of material capable of adsorbing gasses and destroying viral particles; the sensor system comprising one or more gas sensors configured to detect the viral particles and transmit viral detection signals to the control system; the control system comprising a processor programmed to receive the viral detection signals from the sensor system and control the ultraviolet light emitting element based on the viral detection signals by turning the ultraviolet light emitting element on or offs with the sorption box comprising an inner sorption box layer and an outer sorption box layer; with the inner sorption box layer having an outer diameter or width and the outer sorption box layer having an inner diameter or width, with the outer diameter or width of the inner sorption box layer being equal to or less than the inner diameter or width of the outer sorption box layer; with the outer sorption box layer and the inner sorption box layer disposed in a cylindrical configuration such that the inner sorption box layer is disposed within the outer sorption box layer and the outer sorption box layer fits around the inner sorption box layer.

18. The device in claim 6, the sensor system comprising infrared detection sensors configured to detect the number of individuals proximate to the device, encode the number of individuals proximate to the device as proximate individual data, and transmit proximate individual data to the control system, with the processor programmed to control the ultraviolet light emitting element based on the proximate individual data.

19. The device in claim 6, the sensor system comprising sound sensors configured to detect coughing or sneezing sounds, encode the detection of coughing or sneezing sounds as possible infection data, and transmit the possible infection data to the control system, with the processor programmed to control the ultraviolet light emitting element based on the possible infection data.

\* \* \* \* \*